United States Patent [19]

Schapira et al.

[11] Patent Number: 5,635,445
[45] Date of Patent: Jun. 3, 1997

[54] GRANULAR HERBICIDAL COMPOSITION BASED ON AT LEAST AMINOTRIAZOLE

[75] Inventors: Joseph Schapira, Paris; Ange C. Guerin, Le Plessis Bouchard; Jacques Schild, Gennevilliers; Jean-Jacques Fuchs, Deuil La Barre; Jean-Paul Fournials, Cergy Pontoise, all of France

[73] Assignee: CFPI, Gennevilliers, France

[21] Appl. No.: 503,719

[22] Filed: Jul. 18, 1995

[30] Foreign Application Priority Data

Jul. 19, 1994 [FR] France ................... 94 08911

[51] Int. Cl.$^6$ ................... A01N 25/12; A01N 43/653
[52] U.S. Cl. ................... 504/127; 504/130; 504/134; 504/139; 504/274
[58] Field of Search ................... 504/274, 127, 504/130, 139, 134

[56] References Cited

U.S. PATENT DOCUMENTS

| 4,361,436 | 11/1982 | McCarthy et al. | 71/86 |
| 4,936,901 | 6/1990 | Surgant, Sr. et al. | 71/92 |

FOREIGN PATENT DOCUMENTS

| 0378985 | 12/1989 | European Pat. Off. |
| 1248296 | 10/1960 | France |
| 2589325 | 11/1985 | France |
| WO89/00079 | 1/1984 | WIPO |

OTHER PUBLICATIONS

C.R. Worthing et al. "The Pesticide Manual" 1991, British Crop Protection Council, Farnham, GB, pp. 30–31.
Chemical Abstracts, vol. 115, No. 13, Sep. 30, 1991, Columbus, Ohio, US; abstract No. 130058.
Chemical Abstracts, vol. 97, No. 13, Sep. 27, 1982, Columbus, Ohio, US; abstract No. 105521, G. Budoi et al. "Studies on the efficiency of some herbicides applied to a vineyard".
W. Van Valkenburg "Pesticide Formulations" 1973, M. Dekker, New-York, US, Chapter 5, J.A. Polon Formulation of pesticidal dusts, wettable powders and granules, pp. 143–212.

*Primary Examiner*—S. Mark Clardy
*Attorney, Agent, or Firm*—Larson & Taylor

[57] ABSTRACT

Granular herbicidal water-soluble composition based either on aminotriazole alone or on aminotriazole combined with at least one other herbicide selected from the group comprising alkaline, alkaline-earth metal and ammonium thiocyanates, glyphosate, MCPA sodium salt, sulfosate, glufosinate, paraquat and metribuzen. It is provided in the form of granules of cylindrical shape, with a composition and a diameter which are substantially identical from one granule of cylindrical shape to another for a given granular herbicidal composition, the diameter and the length of the said granules of cylindrical shape being respectively of the order of 0.4 to 2 mm, preferably of 0.8 to 1.4 mm, and of the order of 5 to 10 millimeters. The said granular herbicidal composition is obtainable by use of a process according to which aminotriazole, alone or as an intimate homogeneous mixture with at least one other herbicide of the above-identified group, is, if necessary, brought by milling to a suitable particle size, mixed with an amount of water sufficient to ensure its cohesion under a moderate pressure, optionally brought together with a surface-active agent and directed through the orifices of the grid of an extrusion device, the granules of cylindrical shape thus obtained being dried.

8 Claims, No Drawings

GRANULAR HERBICIDAL COMPOSITION BASED ON AT LEAST AMINOTRIAZOLE

The invention relates to a granular herbicidal water-soluble composition based on aminotriazole alone or on aminotriazole in combination with at least one other herbicide selected from the group comprising alkaline, alkaline-earth metal and ammonium thiocyanates, glyphosate, MCPA sodium salt, sulfosate, glufosinate, paraquat and metribuzen.

It also relates to a new industrial product consisting of a specific presentation form of the abovesaid herbicidal composition in which the constituent granules are compacted into blocks.

The expression "granular composition" denotes a solid presentation form which is sufficiently hard to prevent abrasion or crushing under normal storage, transportation and handling conditions.

Aminotriazole, that is to say 1,2,4-triazolylamine, also known as 3-amino-1,2,4-triazole or alternatively 1H-1,2,4-triazol-3-amine, is a herbicide with root and leaf effect capable of inhibiting the synthesis of chlorophyll and the regrowth of buds; it is widely used with success as a selective herbicide on the vine and as a total herbicide on non-agricultural areas; it also possesses an antigermination effect; technical aminotriazole is generally provided in the form of flakes or of a white or greenish or yellowish powder, with a melting point of 149° to 159° C., and a minimum purity of 95%, determined by argentometry; it can be identified according to the CIPAC method No. 90.

Ammonium thiocyanate, taken as an example of alkaline thiocyanate, is generally provided in the form of a white crystalline powder, with a melting point of 140° to 148° C. and a minimum purity of 98 to 99%, determined by argentometry; sodium thiocyanate, as another example of an alkaline metal thiocyanate, is also provided in the form of a white crystalline powder, with a purity of 92 to 96%, but these contents may be slightly decreased due to the fact that, in order to facilitate their handling and to prevent caking under the effect of moisture or pressure, these products receive a coating by a few per cent of filler, for example silica; thiocyanates are non-selective contact herbicides.

It is known, in particular by Patent FR-A-1,248,296, that, during the simultaneous use of aminotriazole and an alkaline thiocyanate, a potentiation of the weed-killing effects of each of the two constituents of the combination occurs.

In other words, when aminotriazole is combined with the thiocyanate ion, lower doses of aminotriazole and markedly lower doses of thiocyanate than those generally required to obtain an acceptable weed-killing effect for each of the products taken separately lead to excellent results; in other words, the combination of aminotriazole and the thiocyanate leads to better results with smaller doses and to a prolonged effect with time.

Herbicidal compositions based on at least aminotriazole, that is to say which can comprise another herbicide and in particular an alkaline thiocyanate, are traditionally presented in the form of concentrated aqueous solutions or in the form of soluble powders.

Neither of these two presentations, in particular when it concerns combinations of aminotriazole and an alkaline thiocyanate, is free from disadvantages.

In the case of presentations in the form of aqueous solutions, the solubility in water of the active materials is limited to approximately 240 g/l for aminotriazole and to 215 g/l for ammonium thiocyanate, in the case of a combination of the two products, the resistance to cold being approximately 0° C.; it is possible to improve the resistance to cold for countries having a severe climate by diluting more, for example to 200 g/l of aminotriazole and to 187 g/l of ammonium thiocyanate or alternatively to 240 g/l of aminotriazole and 55 g/l of ammonium thiocyanate, by acidifying the solution with an inorganic acid; moreover, liquid presentations, in order to form a homogeneous solution, can only accept adjuvants which are soluble in the medium; due to their dilution, aqueous solutions require bulky plastic containers, which are therefore expensive, leading to transportation and storage costs as well as to cleaning and destruction costs after use; moreover, the handlers must take care to avoid any spillages onto the skin and into the eyes and must be able to wash themselves with water as soon as possible; finally, in the case of the acidification of these aqueous aminotriazole and thiocyanate solutions, there is the possible fear of corrosion of the application equipment or of the metal fences which sometimes surround fields.

Presentations in the form of soluble powders overcome some of the disadvantages inherent in aqueous solutions but they can still be improved because they are dusty and the fine powder particles can be carried away and stick to the skin of the handler due to the very high hygroscopicity of ammonium or sodium thiocyanate which rapidly becomes deliquescent on contact with the skin; moreover, presentations in the form of powders have the disadvantage of generating hard and compact lumps, despite the presence of the usual anticaking agents if traces of moisture should have remaining in the powder during manufacture or should be accidentally introducing into the container; finally, they have the disadvantage which lies in the fact that the active materials can experience segregation due to their particle sizes, or to their different densities, in particular under the effect of the vibrations experienced during transportation.

The Applicants, aware of these problems, have already proposed to present, in granular form, herbicidal compositions containing a phytopharmaceutical substance comprising in particular aminotriazole, optionally in combination with other active substances.

It is noticed that herbicidal granular compositions based on other herbicides are already known.

In that connection, EP-A-0 378 985 discloses granular herbicidal water-soluble compositions; the active substance in these compositions is consisting of glyphosate possibly combined to another water-soluble herbicide selected from acifluorfen, chloramben, 2,4-D, endothal, mecoprop, picloram, MCPA, benzac, dicamba, dalapon, MCPB, Pursuit and Scepter.

Furthermore, the patent WO 89/00079 discloses herbicidal granular water-dispersible compositions; the active substance in these water-dispersible compositions is selected from the group comprising cypermethrin, diuron, simazine, atrazine, cyanazine, dalapon-Na, the mixture of simazine with amitrole and dalapon-Na, fluometuron, methazole, metoxuron, norflurazon, oryzalin, hexazinone, the mixture of hexazinone with diuron, metribuzen, thiram, azinphosmethyl, the mixture of metiram with nitrothal-isopropyl, and propargite.

The granular compositions based on aminotriazole already proposed by the Applicant Company are disclosed in the French Patent FR-A-85 16297; they are consisting of granules capable of disintegrating based on aminotriazole alone or in combination with other active substances, especially alkaline thiocyanates, these granules being obtained by successively carring out:

the production of an intimate mixture of the active substances, of a dispersing binder comprising an alkaline or ammonium salt of a condensate of naphtholsulphonate and of resol, of a disintegrating hydrotrope comprising an alkaline or ammonium salt of an alkylbenzenesulphonic acid and optionally of other adjuvants, in the form of a fine homogeneous powder optionally milled on a powder mill before rehomogenization, the granulation in a rotary disc granulator or a vessel equipped with stirrers and systems for breaking up lumps and the drying of the granules.

However, these granules have not been entirely satisfactory.

Consequently, the object of the invention is, above all, to overcome the drawbacks of the prior art.

And the Applicants have the merit of having found that this object is achieved when the granular herbicidal water-soluble composition according to the invention is prepared by directing through the orifices of the grid of an extrusion device either aminotriazole alone or aminotriazole in an intimate homogeneous mixture with at least one other herbicide selected from the group comprising alkaline, alkaline-earth metal and ammonium thiocyanates, glyphosate, MCPA sodium salt, sulfosate, glufosinate, paraquat and metribuzen, after having brought it, if necessary, by milling to a suitable particle size, mixed with an amount of water sufficient to ensure its cohesion under a moderate pressure and optionally brought it together with a surface-active agent, said extrusion operation providing granules of cylindrical shape which are dried.

The result is all the more unexpected and surprising as the highly hygroscopic character of at least some of the herbicides combined with the aminotriazole, especially thiocyanates, would result in a lack of homogeneity due to the absorption of the water necessary for the granulation.

By way of consequence, the granular herbicidal water-soluble composition according to the invention based either on aminotriazole alone or on aminotriazole combined with at least one other herbicide selected from the group comprising alkaline, alkaline-earth metal and ammonium thiocyanates, glyphosate, MCPA sodium salt, sulfosate, glufosinate, paraquat and metribuzen, is characterized in that it is provided in the form of granules of cylindrical shape, with a composition and a diameter which are substantially identical from one granule of cylindrical shape to another for a given granular herbicidal composition, the diameter and the length of the said granules of cylindrical shape being respectively of the order of 0.4 to 2 mm, preferably of 0.8 to 1.4 mm, and of the order of 5 to 10 millimeters, the said granular herbicidal composition being obtainable by use of a process according to which aminotriazole, alone or as an intimate homogeneous mixture with at least one other herbicide of the above-identified group, is, if necessary, brought by milling to a suitable particle size, mixed with an amount of water sufficient to ensure its cohesion under a moderate pressure, optionally brought together with a surface-active agent and directed through the orifices of the grid of an extrusion device, the granules of cylindrical shape thus obtained being dried.

The constituent granules of the abovesaid granular herbicidal composition correspond to the required hardness conditions, have a composition very close to that of the overall composition of the product, are not subject to segregation phenomena and all dissolve largely in the same time.

According to an advantageous embodiment, the granular herbicidal composition in accordance with the invention is provided in the form of blocks, advantageously parallelepipedal blocks, obtained by compacting before drying, under a sufficient pressure, in particular from 0.1 to 10 kPa, a sufficient amount of its constituent granules.

In this specific presentation in which the granules are compacted into blocks, the unit is also sufficiently hard to avoid abrasion or crushing under normal storage, transportation and handling conditions; the blocks have the shape in particular of rectangular parallelepipeds but can also have the shape of cubes, cylinders, spheres, pyramids, cone slices, prisms and others, according to the compression equipment or the mould used for obtaining them; their sizes can range from a few centimeters to a few tens of centimeters in their largest dimension.

The new granular herbicidal composition in accordance with the invention combines the advantages of the presentations in powder form and in solution form without having the disadvantages thereof; they can have a very high concentration of active material, the only limitation being the active material content of the technical product used.

It also makes it possible, when aminotriazole is used in combination with another herbicide of the above-identified group, to vary the proportions of the active materials at will; it is possible, for example, to provide for aminotriazole/ammonium thiocyanate proportions ranging from 95/5 to 40/60, preferably from 54/46 to 70/30, by weight, the problem of resistance to cold of the aqueous solutions not arising.

It is possible to add, to the granular herbicidal composition according to the invention formulation adjuvants capable of improving the herbicidal efficiency by their wetting or penetrating power or by their moisture-retaining power or their ability to withstand leaching due to rain or to dew.

Moreover, the granular herbicidal composition in accordance with the invention is not dusty and, consequently, the risk of contamination via the skin is greatly reduced; the container, which can be a damp-proof paper bag, is completely emptied and can be destroyed after use without risk of still containing active material stuck to its sides.

It is possible to add the other herbicides selected from the above-identified group to the composition according to the invention at the time of the preparation at the time of use in the tank for preparation of the slurry intended for the herbicidal treatment; however, for ease of use or in order to avoid proportioning errors, it is also possible to add these other herbicides to the composition proper in the desired proportions.

In consequently proposing to prepare the granular herbicidal compositions in accordance with the invention, the following or equivalent procedure is used.

The active material, which comprises at least aminotriazole alone or aminotriazole in combination with at least one other herbicide selected from the above-defined group, is first selected.

The preparation is carried out of an intimate and homogeneous mixture of the constituents of the composition existing in the powder state and, if necessary, a milling is carried out in order to arrive at a suitable particle size so that the fundamental particles, while having a size which ensures that they have a fairly short dissolving time, cannot cause blinding of the orifices of the grid of the extrusion device. The liquid products, in particular the surface-active agent, which it is desired to introduce into the formula are then optionally added and homogenization is carried out.

The powder thus obtained is mixed with an amount of water sufficient to ensure its cohesion when it is subjected to a moderate compression; in practice, the value of the pressure applied can be 50 g/cm²; in a variant, this amount of water, conveyed by spraying, makes it possible to introduce an additional amount of surface-active agent which is dissolved beforehand in the water.

The powder thus obtained is extruded through a grid pierced with holes by using an extrusion device; the orifices of the grid have a diameter chosen as a function of the diameter desired for cylindrical vermicelli which are to be obtained; this diameter is generally approximately 1 millimeter. The granules of cylindrical shape obtained have a diameter of the order of 0.6 to 2 mm, preferably of 0.8 to 1.4 mm, and a length which can reach several centimeters, in particular from 5 to 10 cm; they are dried either in an oven, as a thin layer at a temperature of greater than 60° C., or in a sealed chamber into which is introduced a drying agent of the anhydrous calcium chloride or silica gel type, or alternatively in a chamber of the same type placed under partial vacuum in order to accelerate the drying. It is also possible to use a fluidized bed process with an airflow with a temperature greater than 60° C., which has the advantage of reducing, without an additional treatment stage, as desired, the extruded vermicelli to sections of a few millimeters in length. A material of regular structure is thus obtained in which the diameter/length ratio can be adjusted between 1/1 and 1/5.

After the drying, a final grading makes it possible to remove possible agglomerates and fine particles which would give a dusty nature to the product obtained.

The surface-active agent optionally present has the aim of improving the wetting or only slightly foaming power of the treatment slurry prepared at the time of use or of producing a biological effect on the treated plants.

The surface-active agent is preferably of nonionic or anionic type and its proportion with respect to the final composition is from 0 to 11%, preferably from 0 to 3% by weight.

It is advantageously chosen from polyoxyalkylenated fatty alcohols or polyoxyalkylenated alkylphenols, preferably polyoxyethylenated nonylphenols, as far as nonionic surface-active agents are concerned, and from sodium salts of sulphated derivatives of polyoxyalkylenated or non-polyoxyalkylenated fatty alcohols or of polyoxyalkylenated or non-polyoxyalkylenated alkylphenols and from sodium alkyl sulphosuccinates, preferably sodium dioctyl sulphosuccinate, as far as anionic surface-active agents are concerned.

The granular herbicidal compositions in accordance with the invention have, for each constituent granule, an individual composition which is very close to that of the overall composition of the product in its entirety; moreover, for a given granular herbicidal composition in accordance with the invention, the composition and the diameter of the constituent cylindrical granules are substantially identical from one granule to another; for this reason, the dissolution time of the composition is constant; in other words, the dissolution time of the granule is independent of its length and solely a function of the diameter; the conventional notion of particle size therefore disappears, since the dissolution time no longer depends on the mass of the granule.

This dissolution time can be assessed by pouring a mass of 10 grams of the granular herbicidal composition according to the invention into a glass measuring cylinder with a volume of 1 liter filled with town water and by inverting it slowly by 180°, thus allowing the granules to pass alternately from one end of the measuring cylinder to the other. The time for disappearance of the solid particles is recorded; a formulation is judged to be of good quality insofar as the dissolution time does not exceed a few minutes and preferentially two minutes.

The hardness of the granules is assessed empirically by crushing a few granules placed in the hollow of one hand by means of the index finger of the opposite hand; a granule of good quality must not give rise to the formation of dust.

It was observed that the formulations according to the invention are satisfactory from this viewpoint.

The blocks, in particular of parallelepipedal shape, obtained by compacting, in particular under a pressure of 0.1 to 10 kPa, from the granular herbicidal composition in accordance with the invention are particularly advantageous for storage, transportation and determination of given amounts of granular herbicidal composition in accordance with the invention by providing for precut markings, in particular at the surface of these blocks.

The dissolution properties of these blocks are substantially equivalent to those of the individual cylindrical granules, in particular due to their porous structure.

The invention can be still better understood using the non-limiting examples which follow and in which advantageous embodiments are described.

EXAMPLE 1

100 g of milled aminotriazole, of technical quality, are placed in a crystallizing dish and progressively moistened with a fine spray of 12 to 14 ml of water. The mixture is regularly homogenized throughout the operation using a spatula.

The powder thus obtained is capable of compacting under the pressure of the spatula, giving flakes with a thickness of a few millimeters.

This moist powder is forced through a grid pierced with circular holes with a diameter of 1.2 mm, using a rotary extruder, so as to form cylindrical granules in the shape of filaments with a length of a few centimeters, in particular from 2 to 6 cm, and with a diameter of 1.2 mm.

The cylindrical granules obtained are dried in an oven at 80° C. for 4 hours.

They are fragmented into sections with a length of 2 to 6 mm by crushing using a brush on a metal sieve equipped with a mesh with an opening of 0.5 mm, so as to separate simultaneously the fine dust which can be formed during this last operation.

The cylindrical granules thus obtained have a satisfactory hardness and dissolve in approximately two minutes.

EXAMPLE 2

The following are intimately mixed in a beaker using a metal spatula:

94 g of milled aminotriazole of technical quality and 6 g of sodium lauryl sulphate.

The flowing powder obtained is moistened by a fine spray of 10 to 12 ml of water, the mixture constantly being homogenized.

The powder thus obtained has a sufficient consistency to be treated by extrusion through a grid equipped with holes with a diameter of 1.2 mm; cylindrical granules are obtained with a length of a few cm, in particular from 2 to 6 cm.

These granules are dried on a laboratory fluidized bed at a temperature of 70° C. for a period of 20 to 30 minutes.

The mechanical effect of the drying air causes the longest granules to break up, the mean length of the granules then being from 2 to 4 mm; dust removal on a sieve with a mesh opening of 0.5 mm makes it possible to separate the fine dust and to finish with the desired product.

The cylindrical granules thus obtained have a satisfactory hardness and dissolve in approximately two minutes.

EXAMPLE 3

The following are introduced into an impeller disc mill/ mixer:

50 g of technical aminotriazole 47 g of technical sodium thiocyanate and 3 g of surface-active agent based on sodium dioctyl sulphosuccinate (in particular that marketed by the Applicant Company under the tradename Galoryl MT 323).

After homogenization of the powder obtained, the mixture is placed in a crystallizing dish with a diameter of 150 mm and moistening is carried out by fine sprays of water alternating with rehomogenizations using a spatula; the total amount of water added is 6%.

When the mixture becomes sticky, it can be subjected to extrusion through a grid pierced with cylindrical holes with a diameter of 1.2 mm.

The cylindrical granules collected are dried in a closed chamber with a controlled humidity which is less than 20% relative humidity at 22° C.

The fraction which passes through a sieve with a mesh opening of 2.5 mm and which is retained on a sieve with a mesh opening of 0.8 mm is selected.

The cylindrical granules thus obtained have a satisfactory hardness and dissolve in approximately two minutes.

EXAMPLE 4

The following are introduced into a laboratory mill:

100 g of technical aminotriazole 94 g of technical ammonium thiocyanate and 194 g of a homogeneous powder with a particle size of less than 0.25 mm are obtained.

Half of this powder, namely 97 g, is treated with 3 g of surface-active agent based on sodium dioctyl sulphosuccinate (that marketed by the Applicant Company under the tradename Galoryl MT 323), the mixture being mixed in a beaker using a spatula.

Due to the hygroscopic nature of ammonium thiocyanate, the mixture is capable of absorbing atmospheric moisture if the latter is sufficiently high; in the contrary case, moistening can be accelerated by a fine spray of water into the atmosphere lying above the product.

As soon as the product reaches the satisfactory consistency, granulation is carried out by extrusion through a grid pierced with orifices with a diameter of 1.2 mm.

The sticky cylindrical granules obtained are distributed in containers with a square cross-section with a side of 35 mm, so as to form blocks of this size with a thickness of 20 mm.

This operation is carried out by compressing the material as little as possible, the pressure applied being 5 kPa.

The blocks obtained are immediately placed in a dry atmosphere in a vacuum desiccator in which the drying agent is anhydrous calcium chloride.

After twelve hours, they can be handled in a dry atmosphere, that is to say having a relative humidity of less than 35% for a temperature of 22° C., in order then to be packaged in any container in which they are sheltered from moisture.

Their rate of dissolution is assessed by placing a block, the mass of which is approximately 18 g, directly in a 1 liter measuring cylinder according to the procedure described above. The rate in question is such that the block has virtually disintegrated and dissolved after a time which is not substantially greater than that necessary starting from the individual granules, namely approximately two minutes.

EXAMPLE 5

38.65 g of glyphosate in its acid form, with a purity of 97%, 18.625 g of sodium bicarbonate and 4.685 g of water are intimately mixed in a beaker. The mixture is left to react, with periodic rehomogenization, until a constant weight is obtained, which can require several days, depending on the more or less fine particle size of the constituents of the mixture.

The above powder is then intimately mixed with 15 g of sodium lauryl sulphate, 154.8 g of aminotriazole with a purity of 96%, 145.25 g of sodium thiocyanate with a purity of 92.5%, 70.97 g of ammonium sulphate of agricultural quality and 70.45 g of sodium carbonate.

The mixture obtained is finally moistened by addition, in a thin stream and with continuous homogenization using a mixer of household type, of 35 g of water.

The moist powder, which then has the desired consistency, is subjected to extrusion through a grid pierced with holes with a diameter of 0.8 mm.

The cylindrical granules obtained are dried in an oven as a thin stationary bed with a thickness of a few millimeters for a period of 2 hours at a temperature of 60° C. They are graded on a sieve between 2 and 0.6 mm.

The cylindrical granules thus obtained have a satisfactory hardness and dissolve in approximately two minutes.

We claim:

1. Granular herbicidal water-soluble composition based either on aminotriazole alone or on aminotriazole in combination with at least one other herbicide selected from the group consisting of alkaline, alkaline-earth metal and ammonium thiocyanates, glyphosate, MCPA sodium salt, sulfosate, glufosinate, paraquat and metribuzin, the said granular herbicidal water-soluble composition being provided in the form of granules of cylindrical shape, whose composition and diameter are substantially identical from one granule of cylindrical shape to another for a given herbicidal composition, the diameter and the length of the said granules of cylindrical shape being respectively from 0.4 to 2 mm and from of 5 to 10 millimeters, the said granular herbicidal composition being obtained by use of a process comprising selecting aminotriazole alone or in intimate homogeneous mixture with at least one other herbicide of the above-identified group, milling it to a suitable particle size, mixing it with an amount of water sufficient to ensure its cohesion under a moderate pressure and causing it to go through the orifices of the grid of an extrusion device and drying the thus obtained granules of cylindrical shape.

2. Granular herbicidal water-soluble composition according to claim 1, wherein the diameter of the granules of cylindrical shape is from 0.8 to 1.4 mm.

3. Granular herbicidal water-soluble composition according to claim 1, wherein the process for the preparation of the granules of cylindrical shape is carried out in the presence of a surface-active agent.

4. Block consisting of the granular herbicidal water-soluble composition according to claim 1 obtained by a process comprising selecting a sufficient amount of constituent granules of the said granular herbicidal water-soluble composition, compacting the said sufficient amount of granules under a sufficient pressure selected from 0.1 to 10 kPa, thus forming the contemplated block and drying the same.

5. Parallelepipedal block of the granular herbicidal water-soluble composition according to claim 1 obtained by a process comprising selecting a sufficient amount of constituent granules of the said granular herbicidal water-soluble composition, compacting the said sufficient amount of granules under a sufficient pressure selected from 0.1 to 10 kPa, thus forming the contemplated block and drying the same.

6. Granular herbicidal water-soluble composition according to claim 1, based on aminotriazole and alkaline, alkaline-earth metal or ammonium thiocyanate, wherein the weight proportion amino-triazole/thiocyanate (expressed in ammonium thiocyanate) ranges from 95/5 to 40/60.

7. Granular herbicidal water-soluble composition according to claim 1, based on aminotriazole and alkaline, alkaline-earth metal or ammonium thiocyanate, wherein the weight proportion amino-triazole/thiocyanate (expressed in ammonium thiocyanate) ranges from 54/46 to 70/30.

8. Granular herbicidal water-soluble composition according to claim 1, wherein the process for the preparation of the granules of cylindrical shape is carried out in the presence of a surface-active agent selected from the nonionic surface-active agents of the group consisting of polyoxyalkylenated fatty alcohols or polyoxyalkylenated alkylphenols and polyoxyethylenated nonylphenols and from the anionic surface-active agents of the group consisting of sodium salts of sulphated derivatives of polyoxyalkylenated or non-polyoxyalkylenated fatty alcohols or of polyoxyalkylenated or non-polyoxyalkylenated alkylphenols, sodium alkyl sulphosuccinates and sodium dioctyl sulpho-succinate.

* * * * *

UNITED STATES PATENT AND TRADEMARK OFFICE
CERTIFICATE OF CORRECTION

PATENT NO. : 5,635,445
DATED : June 3, 1997
INVENTOR(S) : SCHAPIRA et al

It is certified that error appears in the above-indentified patent and that said Letters Patent is hereby corrected as shown below:

Title page: item [73] should read as follows:

--[73] Assignee: CFPI AGRO, Gennevilliers, France--.

Signed and Sealed this

Thirteenth Day of January, 1998

Attest:

BRUCE LEHMAN

*Attesting Officer*  *Commissioner of Patents and Trademarks*